United States Patent
Nagasawa et al.

(10) Patent No.: US 7,557,216 B2
(45) Date of Patent: Jul. 7, 2009

(54) PROCESS FOR PRODUCTION OF 5-CHLORO-2,4-DIHYDROXYPYRIDINE

(75) Inventors: Hiroshi Nagasawa, Kodama-gun (JP); Katsuyuki Higurashi, Kodama-gun (JP); Etsuji Yamanaka, Chiyoda-ku (JP)

(73) Assignee: Taiho Pharmaceutical Co., Ltd., Tokyo (JP)

( * ) Notice: Subject to any disclaimer, the term of this patent is extended or adjusted under 35 U.S.C. 154(b) by 180 days.

(21) Appl. No.: 11/814,576

(22) PCT Filed: Jan. 25, 2006

(86) PCT No.: PCT/JP2006/301126

§ 371 (c)(1),
(2), (4) Date: Jul. 24, 2007

(87) PCT Pub. No.: WO2006/080339

PCT Pub. Date: Aug. 3, 2006

(65) Prior Publication Data

US 2009/0043101 A1    Feb. 12, 2009

(30) Foreign Application Priority Data

Jan. 26, 2005    (JP) ............................. 2005-018100

(51) Int. Cl.
*C07D 213/09*    (2006.01)
(52) U.S. Cl. .................................. 546/250
(58) Field of Classification Search ............ 546/250
See application file for complete search history.

(56) References Cited

FOREIGN PATENT DOCUMENTS

| JP | 62 155215 | 7/1987 |
| JP | 5 39241 | 2/1993 |
| JP | 5 78324 | 3/1993 |

OTHER PUBLICATIONS

Sato, M. et al.,"Synthesis of 5-Fluoro-1,3-dioxin-4-ones: Versatile Building Blocks of Fluorinated Compounds", J. Chem. Soc., Chem. Commun., No. 10, pp. 699-700, 1991.

Sato, M. et al., "Synthesisi of 5,6-Unsubstituted 1,3-Dioxin-4-ones", Synthesis, No. 2, pp. 224-226, 1985.

H. J. Den Hertog, et al., "The Reactivity of Halogen Atoms Occupying Positions 3 and 5 in 2,4-Dihydroxypyridine", Laboratory of Organic Chemistry, Recueil, No. 73, 1954, pp. 704-708.

C. R. Kolder, et al., "Synthesis and Reactivity of 5-Chloro-2, 4-Dihydroxypyridine", Laboratory of Organic Chemistry, Recueil, No. 72, pp. 285-295 , (1953).

*Primary Examiner*—Rita J Desai
*Assistant Examiner*—John Mabry
(74) *Attorney, Agent, or Firm*—Oblon, Spivak, McClelland, Maier & Neustadt, P.C.

(57) ABSTRACT

To provide an industrially advantageous process for producing 5-chloro-2,4-dihydroxypyridine, which is an inhibitor acting on a biodegradation enzyme that biodegrades an antimalignant-tumor agent 5-fluorouracil. The process is carried out under mild conditions with a small number of steps and produces less industrial waste.

The process employs a 5-chloro-1,3-dioxin-4-one derivative (2) as a starting substance to thereby form a pyrone derivative (4) represented by formula (4):

[F1]

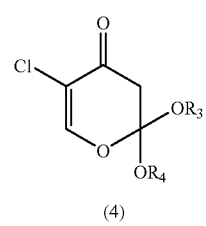

(4)

(wherein $R_3$ and $R_4$, which are identical to or different from each other, each represent a C1 to C6 linear-chain or branched-chain alkyl group, or a silyl group having a C1 to C6 linear-chain or branched-chain alkyl group), and subsequently, 5-chloro-2,4-dihydroxypyridine (1) is produced from the pyron derivative.

2 Claims, No Drawings

PROCESS FOR PRODUCTION OF 5-CHLORO-2,4-DIHYDROXYPYRIDINE

TECHNICAL FIELD

The present invention relates to a process for producing 5-chloro-2,4-dihydroxypyridine, which is useful as an inhibitor of a biodegradation enzyme that biodegrades an anti-malignant-tumor agent 5-fluorouracil exhibiting an excellent anti-tumor effect, and to a pyrone derivative, which is a production intermediate.

BACKGROUND ART

5-Chloro-2,4-dihydroxypyridine (non-proprietary name: Gimeracil) is known to potentiate the anti-tumor activity of 5-fluorouracil (an anti-malignant-tumor agent) by inhibiting dihydropyrimidine dehydrogenase, which is a biodegradation enzyme which acts on 5-fluorouracil (see Patent Document 1). As a commercial product, a 5-fluorouracil-based anti-tumor agent, which is a combination drug of Gimeracil, Tegafur, and Oteracil Potassium, is available on the market as TS-1 (trade name).

Hitherto, the following 5-chloro-2,4-dihydroxypyridine production processes are known. Note that, in the following schemes, symbols "Ac" and "Et" denote an acetyl group and an ethyl group, respectively.

A process disclosed in Non-Patent Document 1 includes a step performed under very severe conditions (i.e., under acidic conditions, in an autoclave at 200° C.), which makes the process industrially unsuitable.

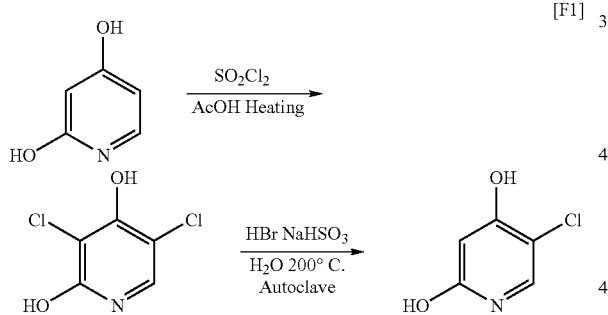

[F1]

A process disclosed in Non-Patent Document 2 includes a large number of steps, which make the process difficult to carry out on an industrial scale.

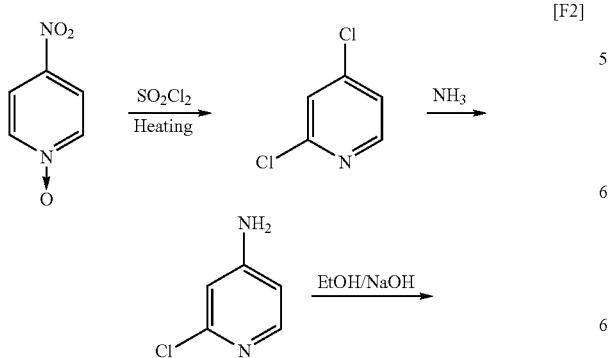

[F2]

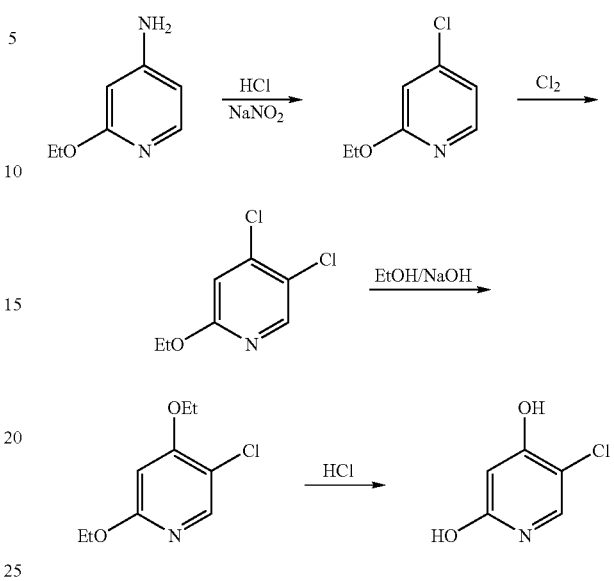

Patent Document 2 discloses a process in which an α,β-unsaturated keto ester derivative is synthesized from malonyl dichloride, and ammonia is reacted with the ester derivative, to thereby produce 2,4-dihydroxy-5-halogenopyridine derivative. In this process, handling of starting materials for producing the α, β-unsaturated keto ester derivative serving as an intermediate is problematic, and there are some problems associated with reaction conditions. For the above reasons the process is difficult to be employed on an industrial scale.

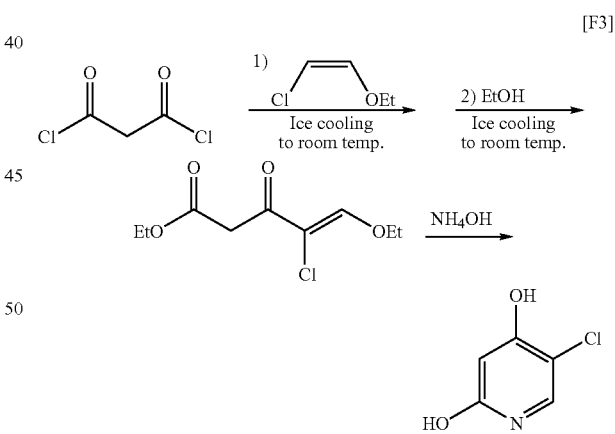

[F3]

Patent Document 3 discloses a process in which the 5-position of 3-cyano-2-hydroxy-3-methoxypiridine is selectively halogenized, and the cyano group is removed through hydrolysis/decarbonation by use of strong acid with heating, to thereby produce 2,4-dihydroxy-5-halogenopyridine derivative. In this method, a large amount of strong acid is employed for hydrolysis, and a large amount of base is employed for neutralizing the strong acid. As a result, a large amount of salts are formed as industrial wastes, which are not preferred from the viewpoint of the environment.

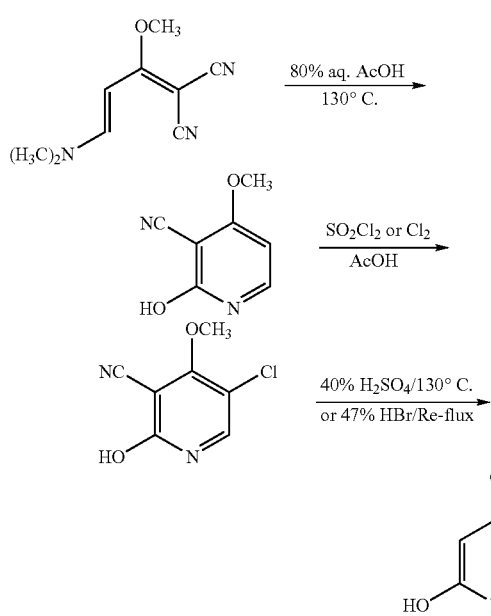

[Patent Document 1] Japanese Patent Application Laid-Open (kokai) No. 62-155215
[Patent Document 2] Japanese Patent Application Laid-Open (kokai) No. 5-39241
[Patent Document 3] Japanese Patent Application Laid-Open (kokai) No. 5-78324
[Non-Patent Document 1] Recueil Des Travaux Chemiques Des Pays-Bas, 1954, Vol. 73, p. 704
[Non-Patent Document 2] Recueil Des Travaux Chemiques Des Pays-Bas, 1953, Vol. 72, p. 285

DISCLOSURE OF THE INVENTION

Problems to be Solved by the Invention

In view of the foregoing, an object of the present invention is to provide an industrially advantageous process for producing 5-chloro-2,4-dihydroxypyridine, which is an inhibitor acting on a biodegradation enzyme that biodegrades an anti-malignant-tumor agent 5-fluorouracil, the process being able to be carried out under mild conditions with a small number of steps and producing less industrial waste.

Means for Solving the Problems

In an attempt to solve the aforementioned problems, the present inventors have carried out extensive studies on the industrial process for producing 5-chloro-2,4-dihydroxypyridine, and have found that a pyrone derivative represented by formula (4) is a remarkably valuable intermediate in production of 5-chloro-2,4-dihydroxypyridine. The present invention has been accomplished on the basis of this finding.

Accordingly, the present invention is directed to a process for producing 5-chloro-2,4-dihydroxypyridine represented by formula (1):

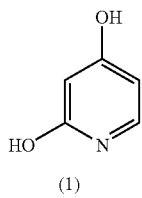

characterized in that the process comprises reacting a 5-chloro-1,3-dioxin-4-one derivative (2) represented by formula (2):

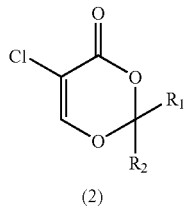

(wherein $R_1$ and $R_2$, which are identical to or different from each other, each represent a C1 to C6 linear-chain or branched-chain alkyl group, or $R_1$ and $R_2$ may be linked to form a C3 to C6 cycloalkane with adjacent carbon atoms) with a ketene acetal derivative (3) represented by formula (3):

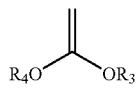

(wherein $R_3$ and $R_4$, which are identical to or different from each other, each represent a C1 to C6 linear-chain or branched-chain alkyl group, or a silyl group having a C1 to C6 linear-chain or branched-chain alkyl group), to thereby form a pyrone derivative (4) represented by formula (4):

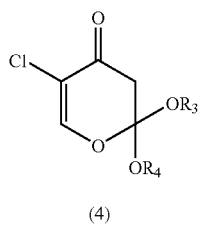

(wherein $R_3$ and $R_4$ have the same meanings as defined above); treating the pyrone derivative (4) with an acid; and subsequently, reacting the product with ammonia.

The present invention is also directed to a pyrone derivative represented by formula (4):

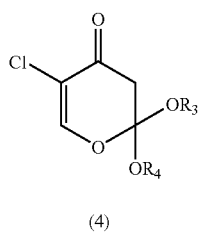

(wherein $R_3$ and $R_4$ have the same meanings as defined above).

EFFECTS OF THE INVENTION

According to the production process of the present invention, 5-chloro-2,4-dihydroxypyridine can be produced under mild conditions, in a simple manner, and with less industrial waste. Thus the process is suited for industrial production. The pyrone derivative, which is the compound according to the present invention, can be isolated and purified, and is remarkably useful as an intermediate for drug production.

BEST MODES FOR CARRYING OUT THE INVENTION

Examples of the C1 to C6 linear-chain or branched-chain alkyl group represented by $R_1$ or $R_2$ in the above formula include methyl, ethyl, propyl, isopropyl, butyl, t-butyl, pentyl, and hexyl. Examples of the C3 to C6 cycloalkane which $R_1$ and $R_2$ may form through linking via adjacent carbon atoms include cyclopropane, cyclobutane, cyclopentane, and cyclohexane. Of these, C3 to C6 cycloalkanes are preferred, with cyclohexane being particularly preferred.

Examples of the C1 to C6 linear-chain or branched-chain alkyl group represented by $R_3$ or $R_4$ in the above formulas include methyl, ethyl, propyl, isopropyl, butyl, t-butyl, pentyl, and hexyl. Examples of the silyl group having a C1 to C6 linear-chain or branched-chain alkyl group include silyl groups each having one to three C1 to C6 linear-chain or branched-chain alkyl groups, which may be identical to or different from one another, the alkyl groups being, for example, methyl, ethyl, propyl, isopropyl, butyl, t-butyl, pentyl, or hexyl. Of these, C1 to C6 alkyl groups are preferred, with ethyl being particularly preferred.

The 5-chloro-1,3-dioxin-4-one derivative (2), serving as a starting substance of the present invention, may be produced through, for example, the following reaction scheme; i.e., treating 1,3-dioxin-4-one derivative (5) with N-chlorosuccinimide in the presence of acetic acid (J. Chem. Soc. Chem. Commun., p. 699 (1991)). Alternatively, the derivative (2) may also be produced through treating 1,3-dioxin-4-one derivative (5) with sulfuryl chloride in the presence of pyridine:

[F10]

(5) → (2)

(wherein $R_1$ and $R_2$ have the same meanings as defined above)

Notably, the aforementioned 1,3-dioxin-4-one derivative (5) is a known compound, and may be readily synthesized through, for example, a method disclosed in "Synthesis, 1985, p. 224-225"; i.e., reaction between a formyl-Meldrum's acid derivative and a ketone or an aldehyde.

The production process of the present invention includes the following two steps (a) and (b):

[step (a)]

[F11]

(5) + (3) →

(4)

(wherein $R_1$ to $R_4$ have the same meanings as defined above).

In step (a), the pyrone derivative (4) according to the present invention is synthesized.

Reaction between a 5-chloro-1,3-dioxin-4-one derivative (2) and a ketene acetal derivative (3) is performed in a solvent.

No particular limitation is imposed on the reaction solvent so long as the solvent does not adversely affect the reaction. Examples of the solvent include aromatic hydrocarbons such as benzene, toluene, and xylene; ethers such as diethyl ether, tetrahydrofuran, and dioxane; and halohydrocarbons such as dichloromethane and chloroform.

The ketene acetal derivative (3) is preferably employed 0.7 to 5 equivalent weight with respect to the 5-chloro-1,3-dioxin-4-one derivative (2).

No particular limitation is imposed on the reaction temperature. The reaction temperature is generally 50° C. to 150° C., preferably 90° C. to 140° C.

No particular limitation is imposed on the reaction time. The reaction time is generally 5 to 120 minutes, preferably 20 to 60 minutes. The compounds represented by formula (4) can be readily isolated and purified through a generally employed isolation/purification method such as column chromatography, distillation, or extraction:

[step (b)]

[F12]

(4) → (1)

(wherein $R_3$ and $R_4$ have the same meanings as defined above).

In step (b), the 5-chloro-2,4-dihydroxypyridine (1), which is a final product of the reaction, is synthesized.

The pyrone derivative represented by formula (4) is treated with acid, and then reacted with ammonia in an excessive amount, to hereby allow ring transformation reaction to proceed.

No particular limitation is imposed on the reaction solvent so long as the solvent does not adversely affect the reaction. Examples of the solvent include alcohols such as methanol and ethanol; ethers such as diethyl ether, tetrahydrofuran, and dioxane; aromatic hydrocarbons such as benzene, toluene, and xylene; halohydrocarbons such as dichloromethane and chloroform; aprotic polar solvents such as acetonitrile, N,N-dimethylformamide, and dimethyl sulfoxide; and water.

In the treatment with acid, known acids may be employed. Examples of the acid include inorganic acids such as hydrochloric acid, hydrobromic acid, sulfuric acid, and nitric acid; organic acids such as formic acid, acetic acid, p-toulene-sulfonic acid, methanesulfonic acid, and trifluoroacetic acid; and acid halides such as acetyl chloride and acetyl bromide, which in situ generate acid in a protic solvent.

No particular limitation is imposed on the amount of the acid employed in the acid treatment. The acid is employed in an amount of 0.01 to 10 equivalent weight, preferably 0.1 to 3 equivalent weight, with respect to the pyrone derivative (4).

No particular limitation is imposed on the reaction temperature. The reaction temperature is generally 0° C. to 100° C., preferably 15° C. to 60° C.

No particular limitation is imposed on the reaction time. The reaction time is generally 5 to 120 minutes, preferably 30 to 90 minutes.

Examples of the ammonia species employed in ring transformation reaction include aqueous ammonia, liquid ammonia, ammonia gas, ammonia dissolved in a solvent to be fed to the reaction system, and ammonia in situ generated in the reaction system.

No particular limitation is imposed on the solvent in which ammonia is dissolved, so long as the solvent does not adversely affect the reaction. Examples of the solvent include aromatic hydrocarbons such as benzene, toluene, and xylene; alcohols such as methanol and ethanol; ethers such as diethyl ether, tetrahydrofuran, and dioxane; halohydrocarbons such as dichloromethane and chloroform; aprotic polar solvents such as acetonitrile, N,N-dimethylformamide, and dimethyl sulfoxide; and water.

In situ generation of ammonia may be carried out through a known method. For example, an inorganic ammonium salt such as ammonium chloride or an organic ammonium such as ammonium acetate may be employed in order to generate ammonia in situ. In addition, a base such as sodium hydroxide or potassium hydroxide may be added.

No particular limitation is imposed on the amount of ammonia. Ammonia is preferably used in an amount of 1 to 30 equivalent weight, with respect to the pyrone derivative (4).

No particular limitation is imposed on the temperature of reaction with ammonia. The reaction temperature is generally 0° C. to 100° C., preferably 15° C. to 60° C.

No particular limitation is imposed on the time of reaction with ammonia. The reaction time is generally 0.5 to 24 hours, preferably 2 to 16 hours.

The thus-produced 5-chloro-2,4-dihydroxypyridine (1) can be isolated through concentration of the reaction mixture and addition of an acid to the residue. Alternatively, the precipitated 5-chloro-2,4-dihydroxypyridine (1) may be isolated as a salt through addition of a base after completion of reaction, and then the salt is treated with an acid, to thereby isolate 5-chloro-2,4-dihydroxypyridine (1). Examples of the salt include salts of an alkali metal such as sodium, potassium, or lithium; and salts of an alkaline earth metal such as magnesium or calcium.

EXAMPLES

Hereinafter, the process for producing 5-chloro-2,4-dihydroxypyridine (1) will be described in more detail by way of Examples and Referential Examples, which should not be construed as limiting the invention thereto.

Referential Example 1

Synthesis of 5-chloro-2,2-dimethyl-1,3-dioxin-4-one

Sulfuryl chloride (2.44 mL, 0.03 mol) was added dropwise to a solution of 2,2-dimethyl-1,3-dioxin-4-one (3.2 g, 0.025 mol) in pyridine (16 mL) under cooling with ice. The mixture was stirred for 30 minutes, while the temperature was maintained, and was further stirred at room temperature for two hours. The reaction mixture was cooled with ice, and water was added to the reaction mixture. The reaction mixture was extracted with dichloromethane, and the formed dichloromethane layer was dried over sodium sulfate anhydrate and concentrated. The concentration residue was purified through silica gel column chromatography (eluent=n-hexane:ethyl acetate=95:5), to thereby yield 2.08 g of the title compound as an oily substance (yield: 51.2%).

$^1$H-NMR (CCl$_4$) δ: 1.73 (s, 6H), 7.23 (s, 1H)

MS m/z: 162 (M$^+$), 164 (M+2)

Referential Example 2

Synthesis of 5-chloro-2,2-cyclohexyl-1,3-dioxin-4-one

Sulfuryl chloride (1.46 mL, 0.018 mol) was added dropwise to a solution of 2,2-cyclohexyl-1,3-dioxin-4-one (2.52 g, 0.015 mol) in pyridine (13 mL) under cooling with ice. The mixture was stirred for 30 minutes, while the temperature was maintained, and was further stirred for two hours at room temperature. The reaction mixture was cooled with ice, and water was added to the reaction mixture. The reaction mixture was extracted with dichloromethane, and the formed dichloromethane layer was dried over sodium sulfate anhydrate, and concentrated. The concentration residue was purified through silica gel column chromatography (eluent=n-hexane:ethyl acetate=95:5), and the obtained oily substance was crystallized from n-hexane, to thereby yield 2.00 g of the title compound (yield: 65.9%).

$^1$H-NMR (CDCl$_3$) δ: 1.21-2.21 (m, 10H), 7.28 (s, 1H)

MS m/z: 202 (M$^+$), 204 (M+2)

Example 1

Synthesis of 5-chloro-2,2-diethoxy-2,3-dihydropyran-4-one

Xylene (10 mL) was added to 2,2-cyclohexyl-5-chloro-1,3-dioxin-4-one (0.91 g, 0.0045 mol), produced in Referential Example 2, and ketene diethyl ether (0.63 g, 0.0054 mol), and the mixture was stirred under heating at 128 to 130° C. (interior temperature) for 40 minutes. The reaction mixture was cooled to room temperature and concentrated. The residue was distilled under reduced pressure, to thereby yield 0.77 g of the title compound (yield: 77.7%).

b.p.: 113-115° C./0.6 kPa $^1$H-NMR (CDCl$_3$) δ: 1.20-1.26 (t, 6H), 3.01 (s, 2H), 3.60-3.78 (q, 4H) 7.48 (s, 1H)

MS (ESI): 221 (M+H), 223 ((M+2)+H)

Example 2

Synthesis of 5-chloro-2,4-dihydroxypyridine

5-Chloro-2,2-dimethyl-1,3-dioxin-4-one (0.49 g, 0.003 mol), produced in Referential Example 1, and ketene methyl (t-butyl)dimethylsilyl ether (0.69 g, 0.0037 mol) were dissolved in dry toluene (7 mL), and the mixture was refluxed under nitrogen for 40 minutes. The reaction mixture was cooled to room temperature, and then concentrated, to thereby yield 0.94 g of 5-chloro-2-methoxy-2-t-butyldimethylsilyloxy-2,3-dihydropyran-4-one. The product was dissolved in dry methanol (25 mL), and acetyl chloride (0.5 mL, 0.007 mol) was added to the solution at room temperature, followed by stirring for one hour. The reaction mixture was concentrated, and methanol (20 mL) was added to the residue. The formed solution was concentrated again, and the residue was dissolved in methanol (25 mL). Concentrated aqueous ammonia (28%) (5 mL) was added to the solution, and the mixture was stirred at 2.5 hours. The reaction mixture was concentrated, and water (5 mL) and acetic acid (0.5 mL) were added to the residue, followed by stirring at room temperature for one hour. The precipitated crystals were collected through filtration, washed with water, and dried under reduced pressure at 40 to 45° C. for 18 hours, to thereby yield 0.16 g of the title compound (yield with respect to 5-chloro-2,2-dimethyl-1,3-dioxin-4-one: 36.5%).

m.p.: 262° C. (decomposition)
$^1$H-NMR (DMSO-d$_6$) δ: 5.72 (s, 1H), 7.51 (s, 1H), 11.31 (br, s, 2H)
MS m/z: 145 (M$^+$)

Example 3

Synthesis of 5-chloro-2,4-dihydroxypyridine

5-Chloro-2,2-dimethyl-1,3-dioxin-4-one (0.32 g, 0.002 mol), produced in Referential Example 1, and ketene diethyl ether (0.28 g, 0.0024 mol) were dissolved in dry toluene (4 mL), and the mixture was refluxed under nitrogen for 40 minutes. The reaction mixture was cooled to room temperature, and then concentrated, to thereby yield 0.39 g of 5-chloro-2,2-diethoxy-2,3-dihydropyran-4-one (yield: 89.0%). The compound (0.23 g, 0.001 mol) was dissolved in ethanol (5 mL), and acetyl chloride (0.1 mL) was added to the solution at room temperature, followed by stirring for one hour. The reaction mixture was concentrated, and the residue was dissolved in ethanol (5 mL). Concentrated aqueous ammonia (28%) (1 mL) was added to the solution, and the mixture was stirred at room temperature for 15 hours. The reaction mixture was concentrated, and water (1.4 mL) and acetic acid (0.14 mL) were added to the residue, followed by stirring at room temperature for two hours. The precipitated crystals were collected through filtration, washed with water, and dried under reduced pressure at 40 to 45° C. for 18 hours, to thereby yield 0.05 g of the title compound (yield with respect to 5-chloro-2,2-diethoxy-2,3-dihydropyran-4-one: 33.0%, yield with respect to 5-chloro-2,2-dimethyl-1,3-dioxin-4-one: 29.4%).

Example 4

Synthesis of 5-chloro-2,4-dihydroxypyridine

Xylene (8 mL) was added to 2,2-cyclohexyl-5-chloro-1,3-dioxin-4-one (0.81 g, 0.004 mol), produced in Referential Example 2, and ketene diethyl ether (0.56 g, 0.0048 mol), and the mixture was refluxed under nitrogen for 20 minutes. The reaction mixture was cooled to room temperature, and concentrated, to thereby yield 0.92 g of 5-chloro-2,2-diethoxy-2,3-dihydropyran-4-one as a concentration residue. The residue was dissolved in ethanol (20 mL), and acetyl chloride (0.5 mL) was added to the solution, followed by stirring at room temperature for one hour. The reaction mixture was concentrated, and ethanol (10 mL) was added to the residue. The mixture was concentrated again, and the residue was dissolved in ethanol (1.4 mL). Concentrated aqueous ammonia (28%) (0.5 mL) was added to the solution, and the mixture was stirred at room temperature for 16 hours. The precipitated crystals were collected through filtration, washed with ethanol, and dissolved in water (5 mL). To the solution, acetic acid (0.5 mL) was added, followed by stirring at room temperature for two hours. The precipitated crystals were collected through filtration, washed with water, and dried under reduced pressure at 40 to 50° C. for 18 hours, to thereby yield 0.31 g of the title compound (yield with respect to 2,2-cyclohexyl-5-chloro-1,3-dioxin-4-one: 53.3%).

Example 5

Synthesis of 5-chloro-2,4-dihydroxypyridine

Xylene (40 mL) was added to 2,2-cyclohexyl-5-chloro-1,3-dioxin-4-one (4.25 g, 0.021 mol), produced in Referential Example 2, and ketene diethyl ether (2.91 g, 0.025 mol), and the mixture was stirred under heating at 128 to 130° C. (internal temperature) for 40 minutes. The reaction mixture was cooled to room temperature, and concentrated. The residue was dissolved in ethanol (60 mL), and at room temperature, acetyl chloride (0.17 g, 0.0022 mol) was added to the solution, followed by stirring for one hour. To the reaction mixture, concentrated ammonia (28%) (4.2 mL) was added, followed by stirring at room temperature for four hours. A 30% aqueous solution of sodium hydroxide (3 g, 0.0225 mol) was added to the reaction mixture, followed by stirring at room temperature for 12 hours. The precipitated crystals were collected through filtration, washed with ethanol (10 mL, two times), and dried under reduced pressure at room temperature for five hours, to thereby yield 3.04 g of a product as crystals. The thus-obtained crystals were dissolved in water (30 mL) under heating, and the solution was cooled to room temperature. 6N Aqueous hydrochloric acid (4.5 g) was added to the solution, followed by stirring at room temperature for five hours. The precipitated crystals were collected through filtration, washed with water, and dried under reduced pressure at 40 to 45° C. for 18 hours, to thereby yield 2.21 g of the title compound (yield with respect to 2,2-cyclohexyl-5-chloro-1,3-dioxin-4-one: 72.4%).

The invention claimed is:

1. A process for producing a 5-chloro-2,4-dihydroxypyridine represented by formula (1):

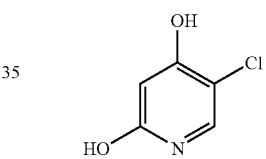

(1)

characterized in that the process comprises reacting a 5-chloro-1,3-dioxin-4-one derivative (2) represented by formula (2):

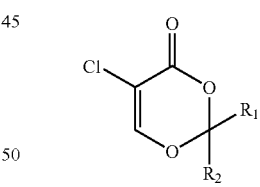

(2)

(wherein $R_1$ and $R_2$, which are identical to or different from each other, each represent a C1 to C6 linear-chain or branched-chain alkyl group, or $R_1$ and $R_2$ may be linked to form a C3 to C6 cycloalkane with adjacent carbon atoms) with a ketene acetal derivative (3) represented by formula (3):

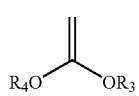

(3)

(wherein $R_3$ and $R_4$, which are identical to or different from each other, each represent a C1 to C6 linear-chain or branched-chain alkyl group, or a silyl group having a C1 to C6 linear-chain or branched-chain alkyl group), to thereby form a pyrone derivative (4) represented by formula (4):

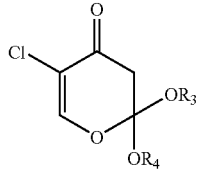

(4)

(wherein $R_3$ and $R_4$ have the same meanings as defined above);

treating the pyrone derivative (4) with an acid; and subsequently, reacting the product with ammonia.

2. A pyrone derivative represented by formula (4):

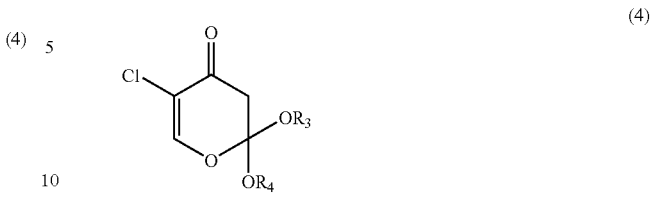

(4)

(wherein $R_3$ and $R_4$, which are identical to or different from each other, each represent a C1 to C6 linear-chain or branched-chain alkyl group, or a silyl group having a C1 to C6 linear-chain or branched-chain alkyl group).

* * * * *